United States Patent [19]

Inaguma et al.

[11] Patent Number: 5,565,773
[45] Date of Patent: Oct. 15, 1996

[54] ARRANGEMENT OF EXCITATION AND DETECTION HEADS FOR DETECTING THE MAGNETIC PROPERTIES OF AN OBJECT

[75] Inventors: Toru Inaguma; Hiroaki Sakamoto, both of Kawasaki, Japan

[73] Assignee: Nippon Steel Corporation, Tokyo, Japan

[21] Appl. No.: 336,207

[22] Filed: Nov. 4, 1994

[30] Foreign Application Priority Data

Nov. 5, 1993 [JP] Japan ................................. 5-301062
Nov. 5, 1993 [JP] Japan ................................. 5-301063

[51] Int. Cl.$^6$ ................................................. G01N 27/72
[52] U.S. Cl. ........................... 324/239; 324/209; 324/262; 73/779
[58] Field of Search ........................... 324/209, 239–242, 324/260–262; 73/578, 763, 779, 862, 325, 862, 331

[56] References Cited

U.S. PATENT DOCUMENTS

| | | | |
|---|---|---|---|
| 3,427,872 | 2/1969 | Leep et al. | 324/209 X |
| 4,408,160 | 10/1983 | King et al. | 324/209 |
| 4,634,976 | 1/1987 | Titto | 324/240 |
| 4,689,558 | 8/1987 | Ruuskanen et al. | 324/209 |
| 4,692,701 | 9/1987 | Dundas et al. | 324/209 |
| 4,881,030 | 11/1989 | Stuecker et al. | 324/209 |
| 4,931,730 | 6/1990 | Olsen et al. | 324/239 X |

FOREIGN PATENT DOCUMENTS

| | | |
|---|---|---|
| 60-57247 | 4/1985 | Japan . |
| 6-194342 | 7/1994 | Japan . |

OTHER PUBLICATIONS

L. R. Karjalainen, et al., IEEE Trans. MAG. Mag16, 514, May 1980.

Nakai, et al. –Iron and Steel, vol. 75, No. 833 (1989) (no month).

Piping Technology, vol. 35, No. 2, 1993, pp. 86–89 (no month).

C. G. Gardner et al., International Journal of Nondestructive Testing 1971, vol. 3, pp. 131–169 (no month).

Primary Examiner—Sandra L. O'Shea
Assistant Examiner—Jay M. Patidar
Attorney, Agent, or Firm—Pollock, Vande Sande & Priddy

[57] ABSTRACT

An arrangement of the magnetic detection and excitation head has an excitation head with a U-shaped excitation core of soft magnetic material forming two legs, each having an end plane facing a surface of a measured object, and an excitation coil wound on the core excitable by a low frequency current; and a detection head with a rod-shaped detection core of non-magnetic or soft magnetic material and a detection coil wound thereon. An end plane of the detection core which is to be close to the surface of the object, and the end planes of the two legs of the excitation core are arranged such that the end plane of the detection core is between the end planes of the two legs and all the end planes are substantially on a common flat plane. Also, a position of the detection head relative to the excitation head is selected such that when an AC current of a predetermined frequency is supplied to the excitation coil, a selected one of a total induced voltage signal, which includes a voltage signal having substantially the same frequency as that of the supplied AC current and a Barkhausen signal induced into the detection coil, and the Barkhausen signal alone is detected.

19 Claims, 9 Drawing Sheets

ARRANGEMENT OF EXCITATION AND DETECTION HEADS FOR DETECTING THE MAGNETIC PROPERTIES OF AN OBJECT

BACKGROUND OF THE INVENTION

1. Field of the Invention

The present invention relates to a magnetic head arrangement and a method of detecting a magnetic property of an object by using the same. More particularly it relates to a magnetic head arrangement used for non-destructive test of properties such as construction, stress and fatigue from the magnetic property of the object and a method of detecting the magnetic property of the object by using the same.

2. Description of the Related Art

It has been attempted to non-destructively test a material of an object by using a nature that a magnetic property of the material depends on a crystal grain size, a construction of precipitates and stress. Namely, when an object is magnetically excited, the magnetization of the object changes and the construction of the object and the state of stress can be detected from the change in the magnetization. For example, a permeability is measured to estimate a tensile strength of a steel or a corecivity is measured to estimate a quenching strength. Recently, a method which uses a Barkhausen noise due to the discontinuity of magnetization has been attracting a notice and a method of estimating a fatigue of mild steel by using such a method (L. P. Karjalainen et al, IEEE Tans. Mag. MAG16, 514(1980)) and a method of estimating a stiffness of tool steel (Nakai et al, Iron and Steel, Vol. 75, No. 833 (1989)) have been proposed.

As methods of magnetically exciting an object, there are known a current passing method, an electric conduction method, a coil method and a yoke method. Among them, the yoke method offers an advantage that it allows relatively simple magnetic excitation by merely applying it to a portion of a relatively large product such as iron or steel products manufactured on line or existing building, and it has been for the test of material. On the other hand, as a method of detecting a change in the magnetization of the object, there are known a coil method, a yoke method, a Hall element method and a reluctance element method. The coil method and the yoke method are convenient since they are less affected by a temperature of the object.

FIG. 8 shows a prior art magnetic head used to detect a magnetic signal and a signal processing system therefor. The magnetic head comprises an excitation head core 51, a detection head core 52, and excitation and detection coils 53 and 54 wound on the respective cores. A material of the excitation head core 51 and of the detection head core 52 is soft magnetic material such as silicon steel, permaloy or soft ferrite.

In order to detect magnetic signal, a ramp wave or an AC sinusoidal wave is supplied from a voltage wave-form generator 58 to the excitation coil through an amplifier 57 and the magnetic head core 51 is brought in contact with the surface of the object 55 to locally magnetize it. A magnetic flux 56 is generated in the magnetized object in the direction of magnetization. When the detection head core 52 having a higher permeability than that of the object is in contact will the surface of the object, a part of the magnetic flux flows into the detection head core and a voltage is induced in the detection coil 54.

A biggest shortcoming of the prior art magnetic head is that when the magnetic head is moved off the object, the strength of the detected magnetic signal abruptly attenuates. This is because a gap is formed between the detection head and the object when the detection head is moved off the object and a magnetic reluctance increases and the magnetic flux 56 no longer flows into the detection core. Accordingly, when the prior art magnetic head is used, the magnetic signal having a high S/N ratio cannot be produced if a distance between the detection head and the object is larger than approximately several tens µm.

Usually, an oxide layer of several tens µm to several hundreds µm is present on the surface of the object. Further, in the on-line measurement, the magnetic head should be spaced from the surface of the object by several hundreds µm for movement in measurement. Accordingly, it is hard to apply the prior art magnetic head to such a circumstance.

JP-A-60-57247 discloses the use of soft ferrite for the magnetic excitation core and the detection head core and an I-shape core for the detection head core. In this patent application, a radius of curvature is imparted to a portion of the core which is to be in contact with the object in order to reduce a measurement error due to a misarrangement thereof when an operator applies the magnetic head to the surface of the object. Accordingly, it is based on the contact measurement and it makes the non-contact measurement difficult because of the attenuation of the signal intensity.

The inventors of the present invention have proposed in JP-A-6-194,342 corresponding to Japanese Patent Application No. 4-357663 a compound magnetic head in which a tip end of the detection head facing the object is formed by a shape variable magnetic material. By using such a magnetic head, the magnetic signal can be detected even if the magnetic head is spaced by approximately 0.2 mm. However, in order to apply it to the on-line test, it is necessary to further increase the allowable distance between the magnetic head and the object.

A total voltage waveform induced by the detection head includes a voltage waveform having the same frequency as that of the excitation superposed with a small high frequency voltage waveform. The total voltage waveform induced in the detection head is herein called a total induced voltage waveform. A permeability and a corecivity may be determined from the total induced voltage waveform. The superimposed small high frequency voltage waveform is called a Barkhausen signal and it is derived from the discontinuous change in the magnetization. Since these magnetic properties have a correlation with the construction of the object, the load stress and the fatigue, they are important parameters in diagnosing the material of the object.

Since the magnitude of the Barkhausen signal waveform is very small relative to the magnitude of the total induced voltage waveform, it is usually impossible to amplify only the Barkhausen signal waveform to a sufficient level within an analysis dynamic range of an oscilloscope 61. Thus, in order to extract only the Barkhausen signal waveform, in the prior art system, a low frequency component of the total induced voltage signal is removed by a frequency filtering device 59 and the resulting signal is amplified by a voltage amplifier 60. Thus, when the prior art magnetic head is used, several additional devices are required to detect the Barkhausen signal, which leads to the increase of the weight and power consumption of the system. Further, as the number of elements increases, more spurious noise is introduced, which makes the measurement of a fine signal more difficult.

For example, Mishima et al detect the waveform of the Barkhausen noise by using a magnetic head having a soft ferrite core. However, it is required to use in the detection system a frequency filtering device because the positional relationship between the excitation head and the detection head is not yet optimized (Piping Technology Vol. 35, No. 2, 1993, pp. 86–89).

Further, C. G. Gardner et al detect the Barkhausen noise by using a magnetic head using an air-core detection coil (International Journal of Non-destructive Testing, 1971, Vol. 3, pp. 131–169). In this case too, the voltage waveform induced in the air-core coil is applied to filtering processing through a frequency filtering device in order to extract the Barkhausen waveform.

SUMMARY OF THE INVENTION

With the prior art magnetic head, it has been difficult to detect the magnetic signal when the magnetic head is spaced from an object to be measured by more than several hundreds μm. In order to make it possible to diagnose the magnetic material such as iron or steel material on production line under operation, a magnetic head which can produce the magnetic signal even when it is spaced from the object by more than several hundreds μm is required.

Accordingly, it is an object of the present invention to provide a magnetic head which permits the detection of magnetic properties of an object to be measured in a non-contact manner.

It is another object of the present invention to provide a method of detecting the magnetic properties of the object by using the above magnetic head.

According to the present invention, a magnetic head for detecting a total induced voltage signal comprises a magnetic excitation head and a detection head. The magnetic excitation head has a U-shaped excitation core of metallic soft magnetic material having two legs, each of which has an end plane adapted to face a surface of an object to be measured, and an excitation coil wound on the excitation core to be excited by a low frequency current. The detection head has a rod-shaped detection core made of non-magnetic material or soft magnetic material and a detection coil wound on the detection core. An wherein an end plane of the detection core of the detection head, which is to be close to the surface of the object, and the end planes of the two legs of the excitation core so are arranged that the end plane of the detection core is disposed between the end planes of the two legs and all the end planes are substantially on a common flat plane, and when defining XY rectangular coordinates on the flat plane such that an X axis of the XY coordinates is defined by a straight line passing centers of gravity, as defined hereinafter, of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values x and y of the XY coordinates representing a position of a center of gravity of the end plane of the detection core satisfy $$0.2a \leq |x| \leq 0.5a, \ |y| \leq 0.8b,$$

where a is a distance between the first and second points and b is a maximum width of the end plane of each of the two legs measured in a direction parallel to the Y axis.

The term "a center of gravity of an end plane of a core" is used throughout the specification and claims to indicate a center of gravity of a thin plate which is an end portion of the core including the end plane of the core and having a very thin uniform thickness, assuming that the core is made of a material having a uniform density distribution. Thus, the position of "the center of gravity of an end plane of a core" is dependent of a shape of the end plane and independent of what material the core is made of.

According to the present invention, a method of detecting a magnetic property of an object comprises the steps of: locating the magnetic head for detecting a total induced voltage signal so as to separate the end planes of the two legs from a surface of the object by a distance in a range of 0.05 to 4 mm inclusive and detecting a total induced voltage signal induced in the detection coil.

According to the present invention, a magnetic head for detecting a Barkheusen signal comprises a magnetic excitation head having a U-shaped excitation core of metallic soft magnetic material having two legs, each of which has an end plane adapted to face a surface of an object to be measured, and an excitation coil wound on the excitation core to be excited by a low frequency current; and a detection head having a rod-shaped detection core made of non-magnetic material or soft magnetic material and a detection coil wound on the detection core. An end plane of the detection core of the detection head, which is to be close to the surface of the object, and the end planes of the two legs of the excitation core are arranged such that the end plane of the detection core is disposed between the end planes of the two legs and all the end planes are substantially on a common flat plane, and when defining XY rectangular coordinates on the flat plane such that an X axis of the XY coordinates is defined by a straight line passing centers of gravity of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values x and y of the XY coordinates representing a position of a center of gravity of the end plane of the detection core satisfy $$|x| < 0.2a, \ |y| \leq 0.8b,$$

where a is a distance between the first and second points and b is a maximum width of the end plane of each of the two legs measured in a direction parallel to the Y axis.

According to the present invention, a method of detecting a magnetic property of an object comprises the steps of: locating the magnetic head for detecting a Barkhausen signal so as to separate the end planes of the two legs from a surface of the object by a distance in a range of 0.05 to 4 mm inclusive and detecting a Barkhausen signal induced in the detection coil.

Further, according to the present invention, a magnetic head for simultaneously detecting a total induced voltage signal and a Barkhausen signal comprises a magnetic excitation head having a U-shaped excitation core of metallic soft magnetic material having two legs, each of which has an end plane adapted to face a surface of an object to be measured, and an excitation coil wound on the excitation core to be excited by a low frequency current; and first and second detection heads. Each detection head has a rod-shaped detection core made of non-magnetic material or soft magnetic material and a detection coil wound on the detection core. End planes of the detection cores of the first and second detection heads, each of which end planes is to be close to the surface of the object, and the end planes of the two legs of the excitation core are arranged such that each of the end planes of the detection cores is disposed between the end planes of the two legs and all the end planes are substantially on a common flat plane, and when defining XY rectangular coordinates on the first plane such that an X axis of the XY coordinates is defined by a straight line passing centers of gravity of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values $x_1$ and $y_1$ of the XY coordinates representing a position of a center of gravity of the end plane of the detection core of the first detection head satisfy $$0.2a \leq |X_1| \leq 0.5a, |y_1| \leq 0.8b,$$

and values $x_2$ and $y_2$ of the XY coordinates representing a position of a center of gravity of the end plane of the detection core of the second detection head satisfy $$|x_2| < 0.2a, |y_2| \leq 0.8b,$$

where a is a distance between the first and second points and b is a maximum width of the end plane of each of the two legs measured in a direction parallel to the Y axis.

According to the present invention, a method of detecting a magnetic property of an object comprises the steps of: locating the magnetic head for simultaneously detecting a total induced voltage signal and a Barkheusen signal so as to separate the end planes of the two legs from a surface of the object by a distance in a range of 0.05 to 4 mm inclusive and simultaneously detecting a total induced voltage signal and 8 Barkheusen signal induced in the detection coil.

DETAILED DESCRIPTION OF THE PREFERRED EMBODIMENTS

Figure 1A:
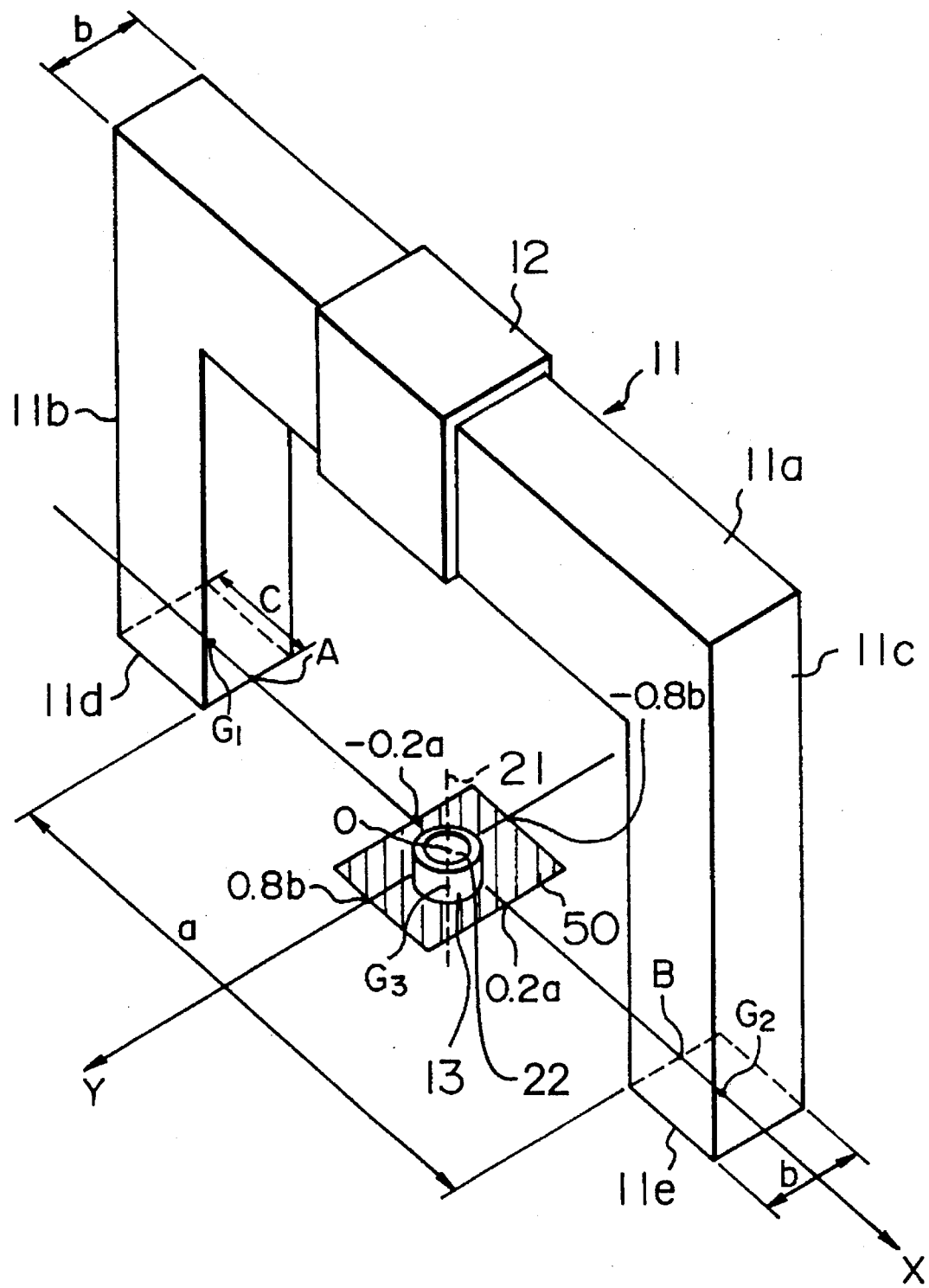
FIG. 1A shows a schematic construction of a magnetic head in one embodiment of the present invention.
Figure 3:
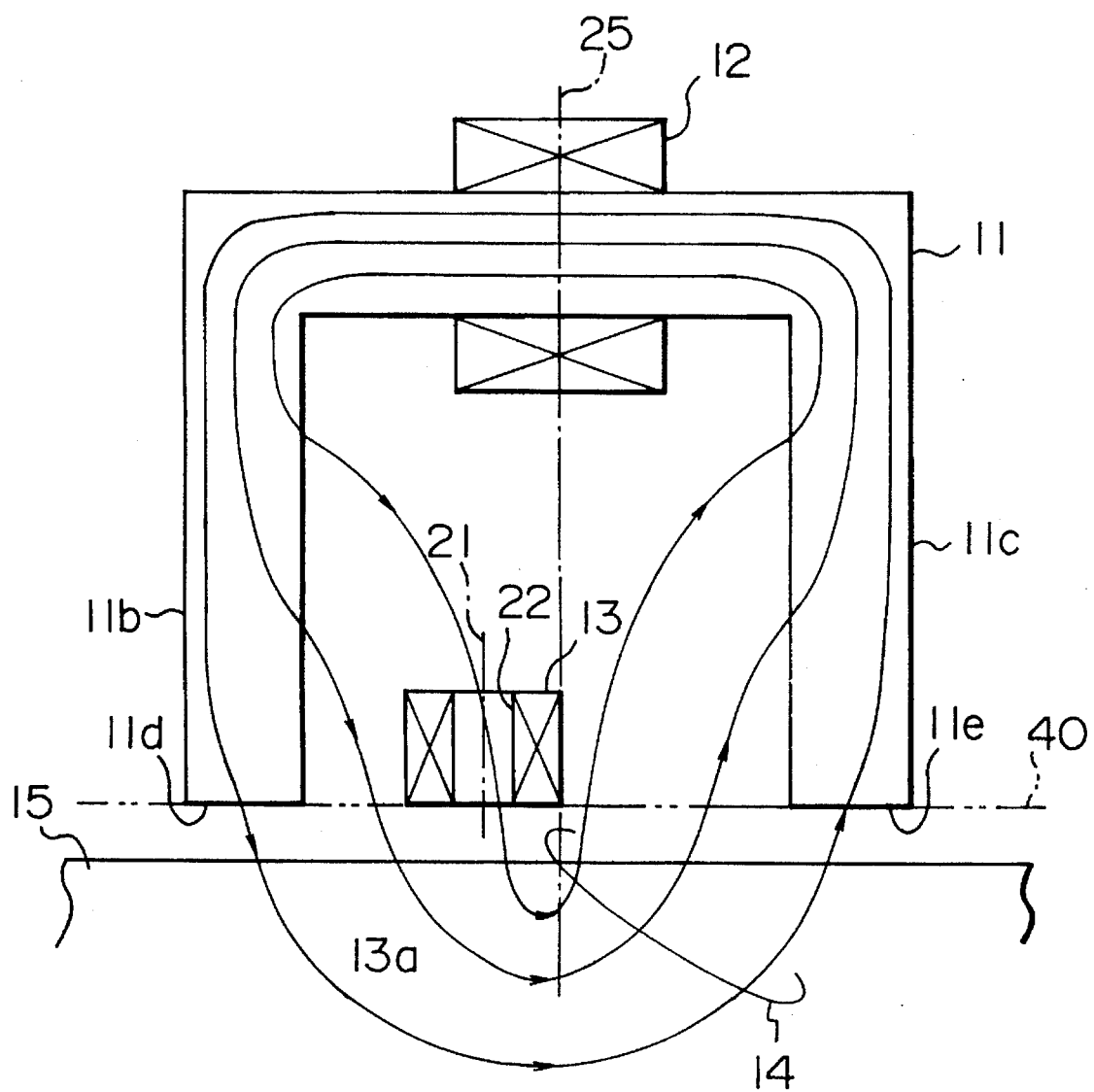
FIG. 3 illustrates a principle of detection of the magnetic properties of the object by the magnetic head of the present invention.

Referring to FIG. 1, the magnetic head of the present invention comprises a U-shaped excitation core 11 made of a soft magnetic material with a rectangular sectional shape and having a center portion 11a and legs 11b and 11c extending from the opposite ends of the center portion symmetrically to a center line 25 thereof (FIG. 3), an excitation coil 12 wound on the center portion 11a to magnetically excite the excitation core 11, and a detection head 13. The detection head 13 includes a detection coil which has an I-shaped or rod-like center core 22 of a non-magnetic material or a soft magnetic material and a winding wound thereon as shown in FIG. 3. The detection head 13 is fixed by an appropriate holding member (not shown) of a non-magnetic material such as synthetic resin at a position between the legs 11b and 11c in such a manner that a center axis 21 thereof is parallel to the center line 25 and an end plane 13a of the detection head is on a common plane 40 with respective end planes 11d and 11e of the legs.

The excitation core 11 is made of a metallic soft magnetic material such as silicon steel or permalloy, and preferably a high saturation magnetization material such as oriented silicon steel sheet so that the object can be sufficiently magnetically excited even if the magnetic head is spaced from the surface of the object. The metallic soft magnetic material excludes a magnetic material of an oxide such as ferrite. A dimension of the excitation core will be described later. The I-shaped core 22 of the detection head 13 generally has a circular or rectangular cross-section but it is not limited thereto. Further, the detection coil of the detection head may be an air-core coil having a center core of air.

When the magnetic head is located, as shown in FIG. 3, in such a manner that the end planes 11d and 11e of the legs and the end plane 13a of the detection coil 13 face the surface of the object 15 to be measured, and an AC current of a predetermined frequency is supplied to the excitation coil, a magnetic flux 14 is produced by the excitation core to flow into the object 15 through the center core 11a and the legs 11b and 11c of the excitation core 11. A part of the magnetic flux 14 which leaks from the inner side surfaces of the legs of the excitation core passes through the center core 22 of the cylindrical detection coil 13 and flows substantially perpendicularly to the surface of the object. The magnetic head of the present invention detects the voltage induced in the detection coil of the detection head by the leakage magnetic flux flowing substantially perpendicularly to the surface of the object. Accordingly, even if the end plane 13a of the detection head is spaced from the surface of the object 15 by several mm, the voltage induced in the detection coil is substantially unchanged and exact detection is attained.

As described above, the excitation core 11 and the detection head 13 are arranged in such a manner that the end planes 11d and 11e of the legs of the excitation core 11 and the end plane 13a of the detection head are on the flat plane 40 as shown in FIG. 3. Now, XY rectangular coordinates are defined on the flat plane such that an X axis is defined by a straight line passing through centers of gravity $G_1$ and $G_2$, as defined hereinbefore, of the end planes 11d and 11e of the legs of the excitation core 11, as shown in FIG. 1, an origin O of the XY coordinates is defined by a center of a line connecting points A and B which are intersections of the X axis with peripheries of the end planes 11d and 11e and a Y axis is defined by a line passing the origin perpendicularly to the X axis.

Further, when designating the distance between the points A and B by a, the maximum width of each end plane of the two legs measured in a direction of the Y axis by b and a thickness of the end plane as measured in a direction of the X axis by c, it is desired that the values of a, b and c satisfy the following conditions 5 mm $\leq$ a $\leq$ 150 mm 1 mm $\leq$ b $\leq$ 50 mm and 1 mm $\leq$ c $\leq$ 50 mm.

This is because it is impossible to assure necessary turns of the excitation coil when a<5 mm, the required excitation power becomes too large when a>150 mm, b>50 mm and c>50 mm. On the other hand, when b<1 mm and c<1 mm, it is difficult to obtain a sufficient magnetic flux.

When each of the two legs has a rectangular cross-section, the value of b is equal to the width of the rectangular cross-section measured in the Y-axis direction.

Figure 2:
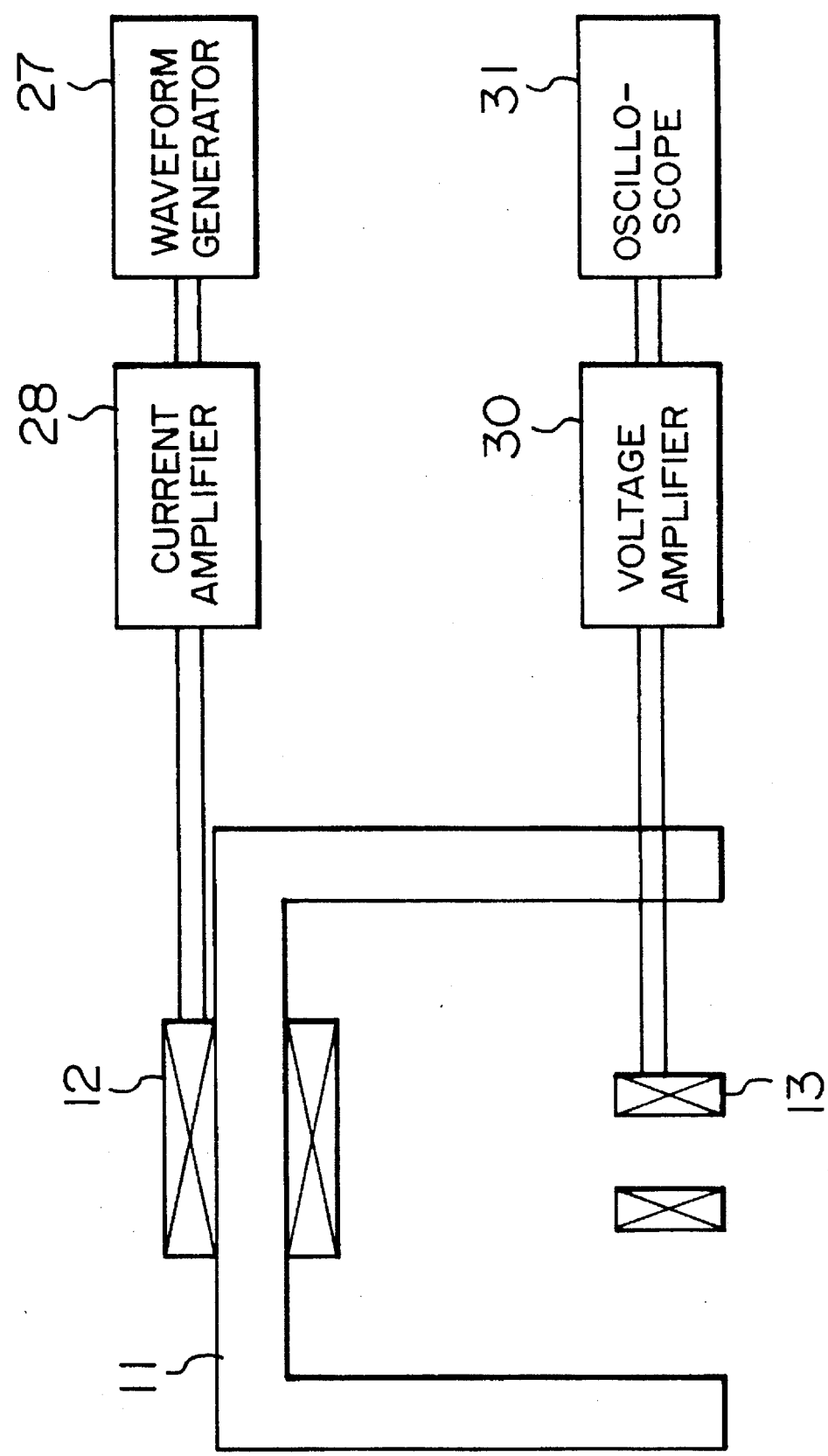
FIG. 2 shows a block diagram of a circuit configuration of a system for measuring magnetic properties of an object by using the magnetic head of the present invention.

FIG. 2 shows a circuit configuration of a system for detecting the magnetic properties of the object by using the magnetic head of the present invention. As shown in FIG. 2, an output voltage of a voltage waveform generator 27 which generates a ramp or sinusoidal wave AC voltage is amplified by an amplifier 28 and applied to the excitation coil 12. On the other hand, the voltage induced in the detection coil 13 is amplified by a voltage amplifier 30 and observed by an oscilloscope 31. As required, the output of the amplifier 30 may be recorded by an appropriate recorder or stored in a memory and subsequently read out for display.

Figure 4:
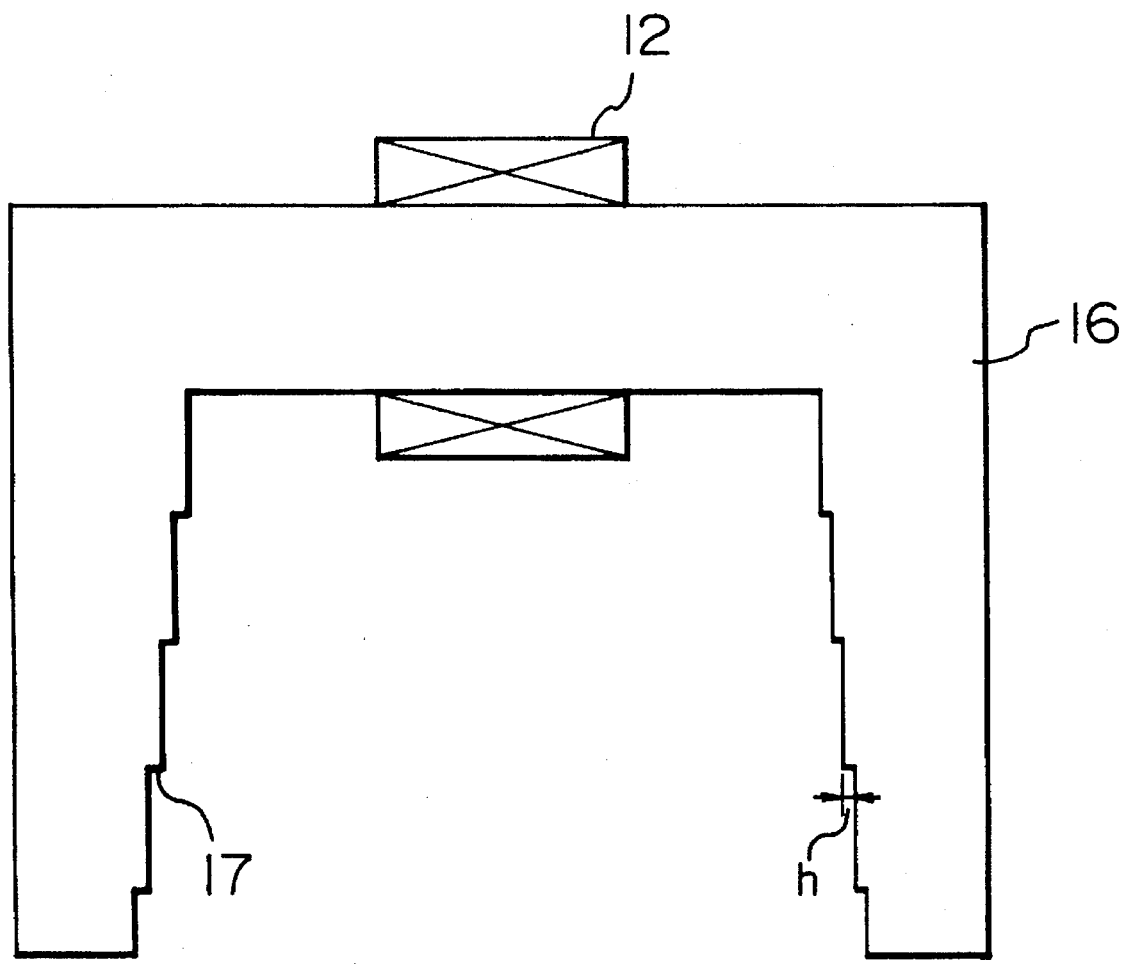
FIG. 4 shows a shape of an excitation core of the magnetic head in other embodiment of the present invention.

The shape of the excitation core 16 is preferably such that the distance a decreases stepwise discontinuously away from the end planes of the legs closest to the object as shown in FIG. 4. With such a shape, the measured magnetic signal voltage increases because the magnetic flux generated substantially perpendicularly to the surface of the object from the inner sides of the legs of the excitation core is larger than that generated when the excitation core having a uniform distance a is used. As to a number of the steps 17, at least one step for each leg is effective to increase the perpendicular magnetic flux, but when it exceeds 1000, it is saturated. Accordingly, the number of steps is preferably in a range of 1 to 1000. As to the height h of the step, the perpendicular magnetic flux is less increased when the height is smaller than 1 μm, and when the step height exceeds 5 mm, it is impossible to uniformly excite the object. Accordingly, the height of the step is preferably in a range of 1 μm to 5 mm. When the shape of the legs of the detection core is made stepwise as mentioned above, a soft magnetic material including ferrite may be used as the core material to attain substantially the same effects as obtained by using an excitation core made of a metallic soft magnetic material with the legs each having an uniform cross-section.

The detection head for detecting the magnetic signal will be now explained.

For the detection coil of the detection head, an air-core coil having an enamel fine wire wound on a center core of a non-magnetic material such as acryl or bakelite may be used. A detection plane of the detection head, that is, the end plane 13a of the center core of the detection head is disposed in parallel to the surface of the object, and fixed between the legs of the excitation head. It is intended to detect the magnetic flux generated perpendicularly to the surface of the object at its area between the legs of the excitation head. By using this detection head, the magnetic signal with a high S/N ratio can be detected even when the detection head is spaced from the object by approximately 4 mm. By using a metallic soft magnetic material for the center core of the detection head, the induced voltage of the magnetic signal can be further enhanced. For example, by using permalloy or Fe or Co amorphous material as the core material, a magnetic head having a higher sensitivity is attained. As the center core of the excitation head, a rod-like core, i.e. I-shaped core extending perpendicularly to the XY-plane in the XY coordinates is used. The center core is made with a circular or rectangular cross-section parallel to the XY-plane. The cross-section is, however, not limited thereto and may be of any shape.

The arrangement of the detection coil will be now explained. In the excitation core described above, the position of the detection coil as fixed between the legs must be determined depending on the application thereof because the magnetic flux distribution significantly changes along the X axis in an area between the legs of the core.

When the XY coordinates are defined as mentioned above, the position of the detection coil can be represented by a position (x, y) on the XY coordinates of the center of gravity $G_3$ of the end plane of the center core of the detection coil facing a surface of the object to be measured. When the center coil has a circular or rectangular cross-section, the center of gravity defined as mentioned hereinbefore coincides with a geometrical center of the circular or rectangular cross-section. Further, when an air-core coil with no core is used, it is assumed that a center core made of air exists in the center of the coil and the position of the detection coil is represented by a position of the center of gravity of the end plane of such a center core. Next, the relationship between the position of the detection coil, which is represented by XY coordinates (x, y), and the voltage signal induced in the detection coil will be explained.

Figure 5:
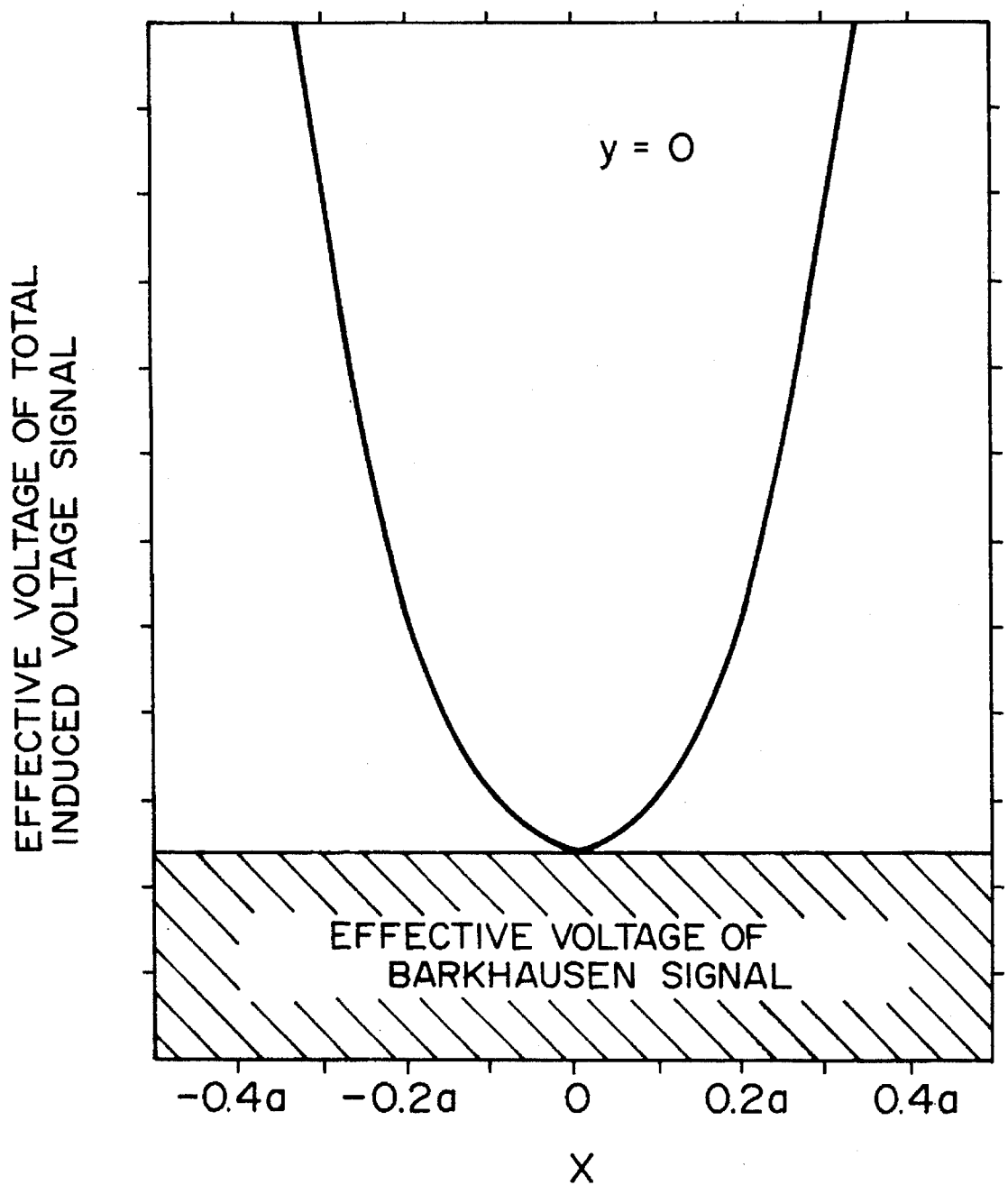
FIGS. 5, 6 and 7 show magnitudes of effective voltages of a total induced voltage signal and a Barkhausen signal detected when the detection coil of the magnetic head of the present invention is located at various positions relative to the excitation core thereof.
Figure 6:
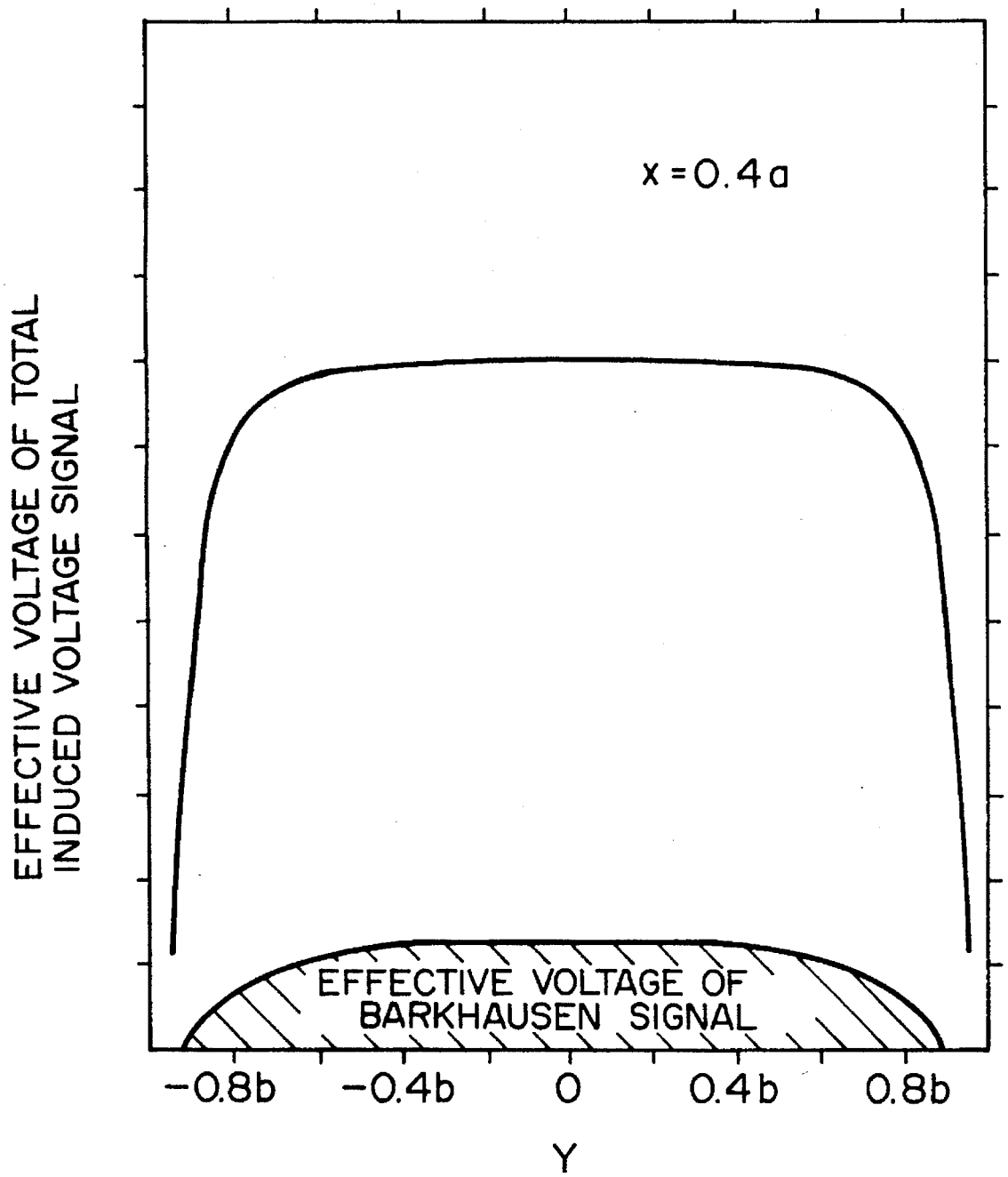
Figure 7:
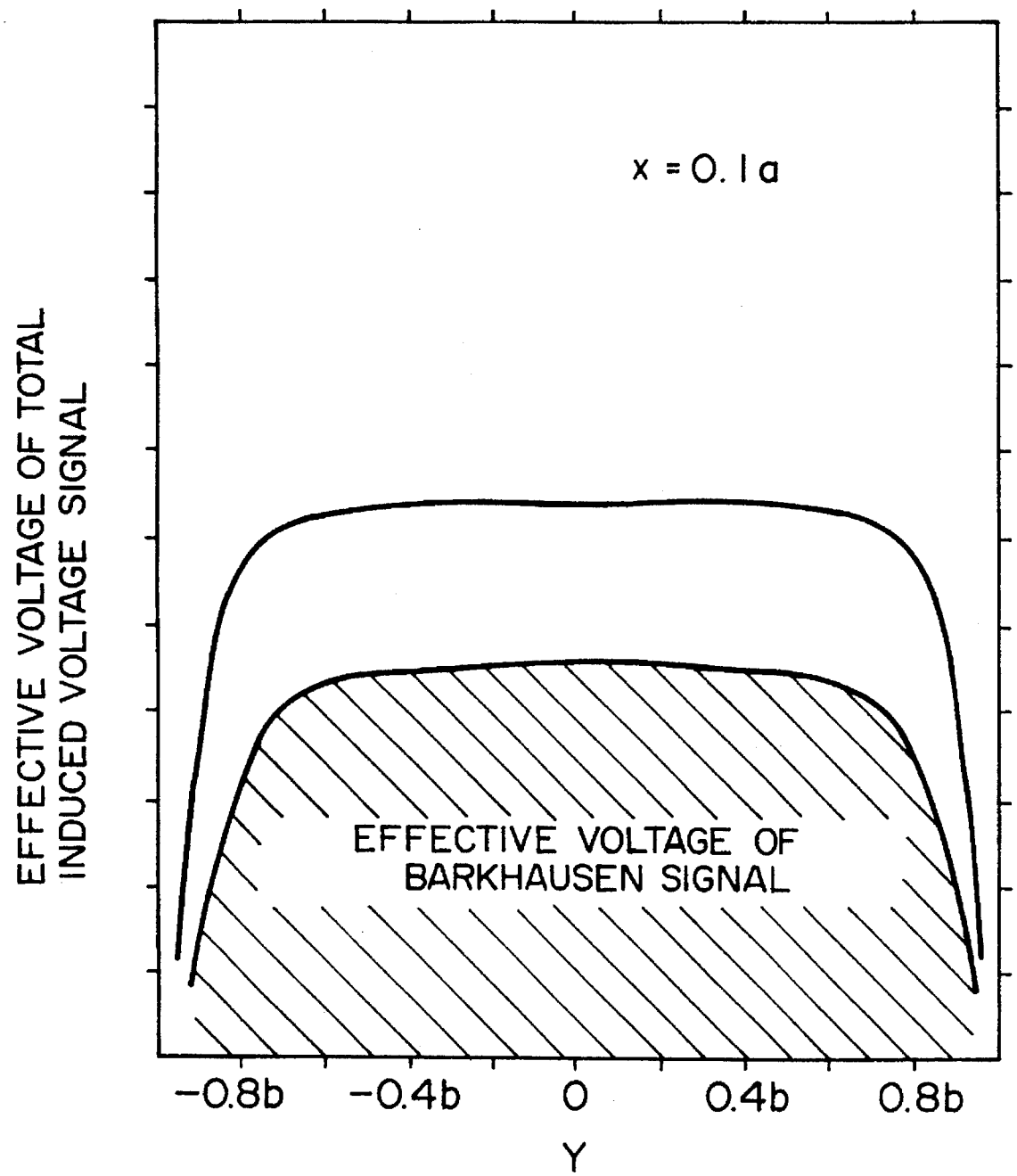
Figure 8:
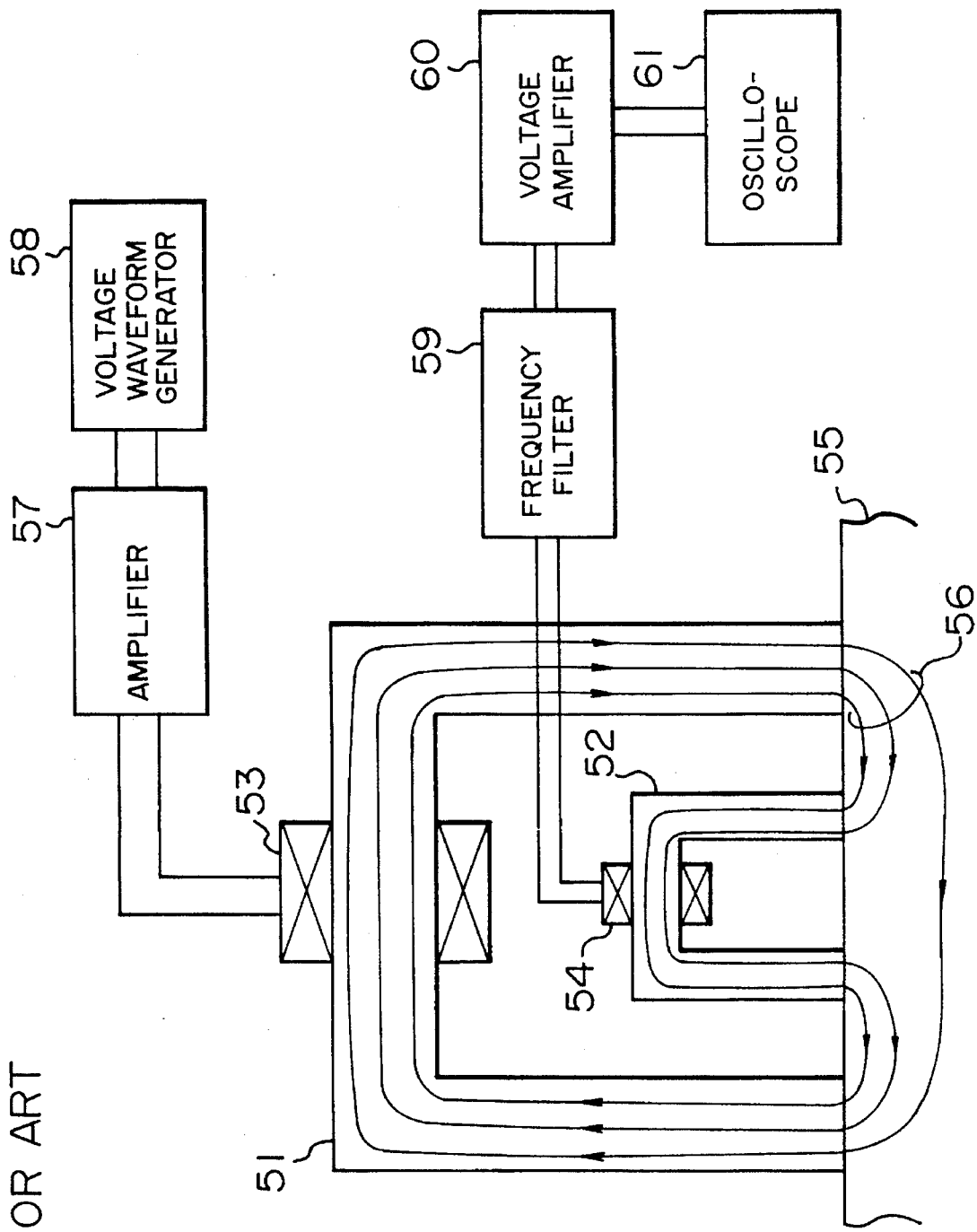
FIG. 8 shows a block diagram of a circuit configuration of a system for detecting the magnetic properties of the object by using a prior art magnetic head.

A total induced voltage signal which is a superposition of a voltage signal waveform having the same frequency as that of the excitation voltage and a small Barkhausen signal having a frequency of several KHz to several hundreds KHz is induced in the detection coil. Information on the material and the load stress of the object can be derived from the total induced voltage signal and the Barkhausen signal, respectively. FIGS. 5, 6 and 7 show the results of investigation about the relationship between the effective voltages of the total induced voltage signal and the Barkhausen signal induced in the detection coil and various positions of the center of gravity of the detection plane of the detection coil. In FIG. 5 where y=0, the total induced voltage is larger as |x| is larger, and minimum in the vicinity of |x|=0. On the other hand, the Barkhausen signal is substantially constant regardless of |x|. When |x| is less than 0.2a, the Barkhausen signal is larger than ⅓ of the total induced voltage. The reason for the total induced voltage being minimum in the vicinity of |x|=0 is that the magnetic flux generated perpendicularly from the surface of the object changes its polarity in the vicinity of |x|=0 and they cancel each other in the detection coil so that the induced voltage is reduced. The reason for the Barkhausen signal being constant is that the signal includes irregular pulses and they do not cancel each other even if the polarity changes. On the other hand, as shown in FIGS. 6 and 7, when |y| is less than 0.8b, both of the total induced voltage signal and the Barkhausen signal exhibit constant values, but when it exceeds 0.8b, they both abruptly decrease, because the detection coil is too much spaced from the excitation core to be sufficiently excited.

By the above reasons, the magnetic head, in which the center of gravity of the detection plane of the detection coil is fixed in an area given by 0.2a≦|x|0.5a and |y|≦0.8b (the hatched area 50 in FIG. 1) and the ratio $V_B/V_A$ of the effective value $V_B$ of the Barkhausen signal voltage to the effective value $V_A$ of the total induced voltage induced in the detection coil is in a range of $0<V_B/V_A≦⅓$, is called as the total induced voltage signal detection head. This magnetic head is used for detection of the total induced voltage signal. When $V_B/V_A$ exceeds ⅓, the measurement of the total induced voltage is affected by the Barkhausen signal. Accordingly, $V_B/V_A$ is set to be ⅓ or less. In the magnetic head in which the detection plane is located at a position where |x| is as close to 0.5a as possible and $V_B/V_A$ is close to 0, a total induced voltage waveform having a high S/N ratio substantially unaffected by the Barkhausen signal is attained.

On the other hand, the magnetic head, in which the center of gravity of the detection plane of the detection coil is fixed in an area given by |x|<0.2a and |y|≦0.8b and the ratio $V_B/V_A$ of the effective value $V_B$ of the Barkhausen signal voltage to the effective value $V_A$ of the total induced voltage induced in the detection coil is in a range of $1/3 < V_B/V_A \leq 1$, is defined as the Barkhausen signal detection head. This magnetic head is used for the detection of the Barkhausen signal. When $V_B/V_A$ is less than 1/3, the detection of the Barkhausen signal is affected by the total induced voltage signal and it is difficult to amplify the Barkhausen signal within the dynamic range of the measurement instrument. Accordingly, $V_B/V_A$ is set to be larger than 1/3. When $V_B/V_A$ is 1, the voltage signal induced in the detection coil includes only the Barkhausen signal, which is most desirable.

Figure 1B:
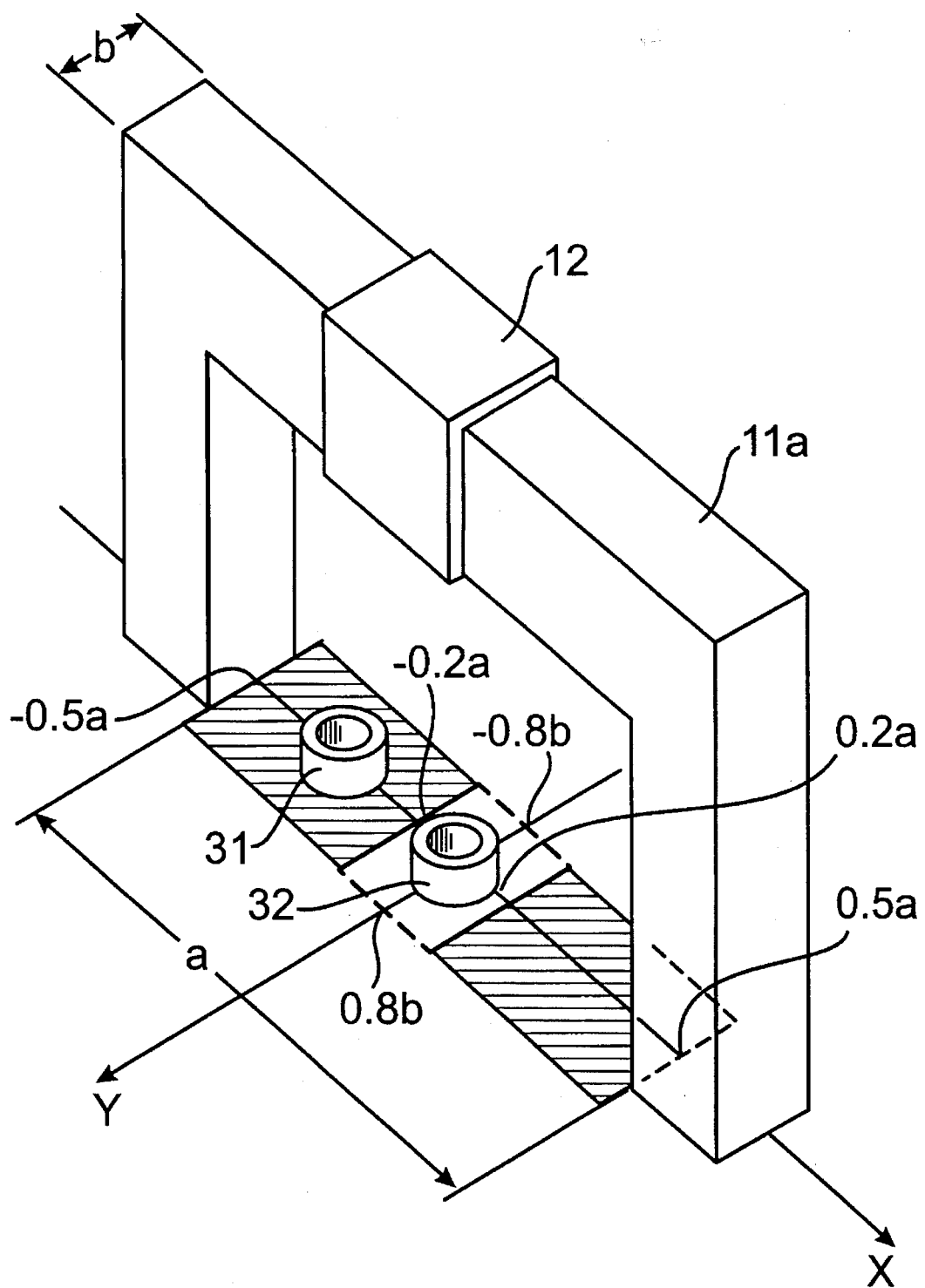
FIG. 1B shows a schematic construction of a magnetic head in another embodiment of the present invention.

In another embodiment of the present invention, as shown, for example, in FIG. 1B the detection head includes two independent detection coils 31, 32 for simultaneously detecting the total induced voltage signal and the Barkhausen signal, respectively. The two detection coils are arranged such that the detection planes thereof are parallel to the surface of the object and the centers of gravity of the detection planes are positioned as follows: The center of gravity of the detection plane of the first detection coil is fixed in an area of $0.2a \leq |x| 0.5a$ and $|y| \leq 0.8b$ so that the ratio $V_B/V_A$ of the effective value $V_B$ of the Barkhausen noise signal to the effective value $V_A$ of the total induced voltage induced in the first detection coil is in a range of $0 < V_B/V_A \leq 1/3$. The center of gravity of the detection plane of the second detection coil is fixed in an area of |x|<0.2a and |y|≦0.8b relative to the excitation head so that the ratio $V_B/V_A$ of the effective value $V_B$ of the Barkhausen signal voltage to the effective value $V_A$ of the total induced voltage induced in the second detection coil is in a range of $1/3 < V_B/V_A \leq 1$. In the actual material test, both signals are simultaneously detected and the information derived therefrom are evaluated in combination. The precision of the diagnosis of the material is significantly improved by the complex evaluation using this magnetic head.

By using the magnetic head of the present invention, the magnetic signal having a practically high S/N ratio is attained even when the magnetic head is spaced from the object by a distance of 0.05 mm to 4 mm.

Experiment 1

A result of the experiment in which the total induced voltage signal is detected using the total induced voltage signal detection head of the present invention while changing the distance between the detection coil and the surface of an object to be measured is shown below. The object was a square bar of 40 mm×30 mm×15 mm of low carbon steel, and its plane of 40 mm×30 mm was used as the object surface. Namely, the magnetic head was arranged to face the plane of 40 mm×30 mm.

The excitation head core is made of a lamination of silicon steel sheets and the dimension of the core is such that the inner distance a of the legs is 20 mm and the thickness b of the core measured in a direction normal to the direction of a is 10 mm. The excitation was done by applying a sinusoidal wave current having a frequency of 2.5 Hz. Since the excitation power changes as the distance between the excitation head and the object increases, a sensor coil was used to control the excitation current so that the excitation power was kept constant.

There were prepared two kinds of detection coils, one being an air-core coil having an acryl core and a coil of enamel fine wire wound on the core and the other being a permalloy-core coil having an I-shaped permalloy core having the same size of detection plane as that of the air-core coil and a coil wound thereon with the same number of turns as that of the coil of the air-core coil. Each of the detection heads was disposed so as to have its detection plane disposed in parallel to the object surface. The position of the center of gravity of the detection plane relative to the excitation head is fixed at a position (x=−4.5; y=0) within an area of 4 mm ≦|x|≦10 mm and |y|≦8 mm.

For comparison purpose, the following two magnetic heads were prepared as controls. One is a combination of a detection head with a conventional U-shape permalloy core having a coil wound thereon and an excitation head having a silicon steel sheet core of the same sectional area as that of the excitation core of the test magnetic head. The detection head was disposed such that the line connecting the legs of the excitation core was parallel to the X axis and the center of gravity of the detection plane of the detection core was at a position (−4.5, 0) on the XY coordinates. The other magnetic head was a combination of a detection head having a coil wound on an I-shape soft ferrite core and an excitation head having an excitation coil wound on a U-shape soft ferrite core having the same dimension as that of the excitation core of the test magnetic head. The detection head was fixed such that the center of gravity of the detection plane of the detection core was at a position (−4.5, 0).

The voltages induced by the respective detection heads were amplified by an amplifier at the same amplification factor and the waveforms were analyzed by an oscilloscope.

Table 1 shows the effective voltages of the total induced voltage signals detected when the distances between the surface of the object and the respective magnetic heads were changed.

TABLE 1

|  | Excitation Head | Detection Head | Distance from Object in mm | Effective Voltage in mV |
|---|---|---|---|---|
| Test 1 | Silicon steel sheet core | Air-core coil | 1.0 | 187 |
| Test 2 | Silicon steel sheet core | Air-core coil | 2.0 | 130 |
| Test 3 | Silicon steel sheet core | Air-core coil | 4.0 | 125 |
| Test 4 | Silicon steel sheet core | I-shape permalloy core | 4.0 | 260 |
| Control 1 | Silicon steel sheet core | U-shape permalloy core | 1.0 | 35 |
| Control 2 | Silicon steel sheet core | U-shape permalloy core | 2.0 | 12 |
| Control 3 | Silicone steel sheet core | U-shape permalloy core | 4.0 | 3 |
| Control 4 | Soft ferrite core | I-shape ferrite core | 1.0 | Not detectable |

As shown in Tests 1 to 3, when the magnetic head of the present invention was used, the total induced voltage signal having the sufficiently high voltage was produced even when the distance between the surface of the object and the magnetic head was 1.0 mm to 4.0 mm. On the other hand, for the magnetic head using the U-shape permalloy as the detection head core, the induced voltage abruptly dropped when the magnetic head was spaced from the surface of object. The reason therefor is that the magnetic flux is hard to flow into the U-shape permaloy core when it is spaced from the surface of object. In the magnetic head using the soft ferrite as the core material, the total induced voltage signal was not detectable when it was spaced by 1 mm.

Experiment 2

The change in the detection signal when the fixed position of the air-core coil was changed while using the same combination of the excitation head and the air-core coil as that used in the previous experiment was studied.

The voltages induced in the respective detection coils were amplified by the voltage amplifier at the same amplification factor and the waveforms were analyzed by the oscilloscope. The Barkhausen signal (BHN) in a frequency range of 1 KHz to 200 KHz was separated by using the frequency filtering device and the effective value thereof was determined. The distance between the magnetic head and the object was 1 mm. Table 2 shows the result.

TABLE 2

| | Magnetic Head | Position of Center of gravity of Air-core coil | Total Induced Voltage $V_A$ in mV | BHN Signal Voltage $V_B$ in mV | $V_B/V_A$ |
|---|---|---|---|---|---|
| Test 5 | Total induced voltage detection | (4.5, 0) | 203 | 35 | 0.17 |
| Test 6 | Total induced voltage detection | (6, 2) | 450 | 36 | 0.08 |
| Test 7 | BHN signal detection | (1.5, 0) | 38 | 35 | 0.92 |
| Test 8 | — | (3, 2) | 71 | 34 | 0.48 |
| Control 5 | — | (6, 12) | 14 | ~0 | ~0 |
| Control 6 | — | (3, 10) | 2 | ~0 | ~0 |

As shown in Tests 5 and 6, when the position of the center of gravity of the detection plane of the air-core coil was in an area of 4 mm≦|x|≦10 mm and |y|≦8.0 mm in accordance with the present invention, the total induced voltage having the high effective voltage was produced. In this magnetic head, the ratio $V_B/V_A$ of the Barkhausen signal to the total induced voltage is small and the affect of the Barkhausen signal may be neglected. In the control 5 in which the center of gravity of the detection plane of the air-core coil is fixed to a position of |y|>8.0 mm, the effective voltage of the total induced voltage signal is significantly low.

As shown in Tests 7 and 8, when the position of the center of gravity of the detection plane of the air-accordance coil was in an area of |x|<4 mm and |y|≦8.0 mm in accordance with the present invention, the ratio $V_B/V_A$ of the Barkhausen signal to the total induced voltage was large. Namely, the Barkhausen signal can be detected substantially independently of the total induced voltage signal. In control 6 in which the center of gravity of the detection plane of the air-core coil was fixed to a position of |y|>8.0 mm, the Barkhausen signal could not be detected.

From the above results, it is seen that the magnetic head fixed in the range of the present invention allows the independent detection of the total induced signal or the Barkhausen signal.

Experiment 3

The Barkhausen signal was detected by using a U-shape excitation head core with steps formed inside the legs. The steps are formed such that the distance a between the inner sides of the legs decreases discontinuously away from the end planes closest to the object. Three types of stepped cores were prepared. The core 1 has 100 steps with a step height h being 10 μm as measured in the direction of a. The core 2 has 10 steps with the step height being 200 μm. The core 3 has one step with the step height being 2 mm. For comparison purpose, a core with no-step was prepared as control. The core material was lamination of silicon steel sheets and the core dimension was such that the distance a between the inner sides of the legs at the end planes of the excitation head closest to the object was 20 mm, and the thickness b of the core measured in a direction normal to the direction of a was 10 mm. The maximum thickness of the core leg measured in the direction of a was equal for all excitation cores. The excitation was done by supplying a sinusoidal wave current having a frequency of 100 Hz to the coil.

The detection coil was an air-core coil having an enamel fine wire wound on the acryl core. The air-core coil was arranged such that the detection plane was parallel to the object surface. In the experiment, the air-core coil was disposed such that the center of gravity of the detection plane of the detection coil was in an area of |x|<4 mm and |y|≦8.0 mm with the ratio $V_B/V_A$ of the Barkhausen signal voltage $V_B$ to the total induced voltage $V_A$ being 1.

A low carbon steel of 100 mm×100 mm×15 mm was used as the object and its plane of 100 mm×100 mm was the object surface to be measured. The above three types of heads were used to detect the Barkhausen signals. The result is shown in Table 3.

TABLE 3

| | Step height in μm | Number of steps | Effective Voltage in mV |
|---|---|---|---|
| Excitation head 1 | 10 | 100 | 173 |
| Excitation head 2 | 200 | 10 | 180 |
| Excitation head 3 | 2000 | 1 | 165 |
| Control 7 | None | None | 110 |

As shown with the excitation heads 1, 2 and 3, the effective voltage of the detected Barkhausen signal becomes larger by forming the steps in the inner sides of the legs of the excitation core. The same experiment was made for the total induced voltage signal having the same frequency as that of the excitation current and the signal voltage was further enhanced by using the excitation core with the steps.

Experiment 4

An experiment was done with respect to the detection of the total induce voltage signal and the Barkhausen signal simultaneously and independently by using the magnetic head of the present invention.

The excitation head cores used were the U-shape core with steps in the inner sides of the legs and the U-shape core with no steps. In the core with the steps, the distance a between the inner sides of the legs discontinuously decreases by 200 μm in each step as it goes away from the end planes closest to the object, and the number of steps is ten. The core material was a lamination of silicon steel sheets and the dimension of the core was such that the distance a between the inner sides of the legs at the end planes closest to the object was 20 mm, and the thickness b of the core measured in a direction normal to the direction of a was 10 mm. The excitation coils of the same number of turns were wound on the two types of heads 31, 32 respectively.

Two air-core coils, each having an enamel fine wire wound on an acryl core, were prepared. Two air-core coils have the detection planes of the same size and the coil windings of the same number with turns. Each air-core coil was disposed such that its detection plane was parallel to the object surface. In the experiment, the first air-core coil was fixed such that the center of gravity of the detection plane was in an area of 4 mm $\leq |x| \leq 10$ mm and $|y| \leq 8$ mm, and the second air-core coil was fixed such that the center of gravity of the detection plane was in an area of $|x|<4$ mm and $|y|\leq 8.0$ mm. A low carbon steel of 100 mm×100 mm×15 mm was used as the object to be measured and its plane of 100 mm×100 mm was selected as the object surface. The excitation was made by supplying a sinusoidal wave current having a frequency of 2.5 Hz to the excitation coil. The voltage waveforms induced by the first detection coil and the second detection coil were amplified at the same amplification factor and the waveforms were analyzed by the oscilloscope.

Table 4 shows the effective voltages of the total induced voltage signals and the Barkhausen signals simultaneously measured by using the respective magnetic heads.

TABLE 4

| | Excitation Head | Air-core Coil 1 | | | Air-core Coil 2 | | |
| --- | --- | --- | --- | --- | --- | --- | --- |
| | | Position of Center of Gravity in mm | $V_b/V_A$ | Total induced Voltage in mV | Position of Center of Gravity in mm | $V_B/V_A$ | BHN Signal in mV |
| Test 9 | Stepped core | (6.5, 0) | 0.06 | 947 | (1.3, 0) | 0.98 | 55 |
| Test 10 | No-step core | (7, 0) | 0.05 | 700 | (1.5, 0) | 0.96 | 36 |

As seen from Tests 9 and 10, the total induced voltage signal and the Barkhausen signal can be simultaneously and independently detected by using the stepped excitation core and the excitation core without steps.

From the above result, it is seen that the magnetic head of the present invention can detect the total induced voltage signal and the Barkhausen signal simultaneously and independently.

By using this magnetic head, a stress of a carbon steel was measured. The measurement error was decreased compared to the measurement by the magnetic head using one air-core coil and the precision was also improved.

By using the magnetic head of the present invention, the detection of the magnetic signal at a position spaced from the surface of an object to be measured by several mm, which was difficult to attain by using a prior art magnetic head, can be attained. Since the present magnetic head produces the magnetic signal in the non-contact manner, it is applicable to the on-line diagnosis of a material for example in an iron and steel manufacturing process and the diagnosis of the steel construction. The on-line diagnosis technique in the iron and steel process is useful for improvement of not only the efficiency in quality management and the precision of products but also the yield of products and hence it is very important. The material diagnosis of the steel construction is an essential technology to assure the safety and accident prevention.

The magnetic head of the present invention can detect the total induced voltage signal and the Barkhausen signal simultaneously and independently. By detecting the magnetic signals of different types independently and simultaneously, the precision in diagnosis of the material is greatly improved. Further, no special unit such as the frequency filter is required for the signal processing, the processing system can be made of smaller size and lighter and the workability in transporting the system is improved. In addition, the electric power is saved and the frequency of maintenance when the system is operated by a battery is reduced and the maintenance manpower is reduced.

We claim:

1. A magnetic head for detecting a total induced voltage signal comprising:

a magnetic excitation head having a U-shaped excitation core of metallic soft magnetic material having two legs, each of which has an end plane adapted to face a surface of an object to be measured, and an excitation coil wound on the excitation core to be excited by a low frequency current; and a detection head having a detection core made of non-magnetic material or soft magnetic material and a detection coil wound on the detection core;

wherein an end plane of the detection core of the detection head, which is to be close to the surface of the object, and the end planes of the two legs of the excitation core are arranged such that the end plane of the detection core is disposed between the end planes of the two legs and all the end planes are substantially on a common flat plane, and when defining XY rectangular coordinates on the flat plane such that an X axis of the XY coordinates is defined by a straight line passing through centers of gravity of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values x and y of the XY coordinates representing a position of a center of gravity of the end plane of the detection core satisfy $0.2a \leq |x| \leq 5a$, $|y| \leq 0.8b$, where a is a distance between the first and second points and b is a maximum width of the end plane of each of the two legs measured in a direction parallel to the Y axis.

2. A magnetic head according to claim 1, wherein the two legs of said excitation core are formed in a step-like shape such that a distance, as measured in a direction of the X axis, between cross-sections of the two legs along a parallel plane parallel to said common flat plane is discontinuously decreased as the parallel plane is further separated from said common flat plane.

3. A magnetic head for detecting a Barkhausen signal comprising:

a magnetic excitation head having a U-shaped excitation core of metallic soft magnetic material having two legs, each of which has an end plane adapted to face a surface of an object to be measured, and an excitation coil wound on the excitation core to be excited by a low frequency current; and a detection head having a detection core made of non-magnetic material or soft magnetic material and a detection coil wound on the detection core;

wherein an end plane of the detection core of the detection head, which is to be close to the surface of the object, and the end planes of the two legs of the excitation core are arranged such that the end plane of the detection core is disposed between the end planes of the two legs and all the end planes are substantially on a common flat plane, and when defining XY rectangular coordinates on the flat plane such that an X axis of the XY coordinates is defined by a straight line passing through centers of gravity of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values x and y of the XY coordinates representing a position of a center of gravity of the end plane of the detection core satisfy $$|x|<0.2a,\ |y|\leq 0.8b,$$

where a is a distance between the first and second points and b is a maximum width of the end plane of each of the two legs measured in a direction parallel to the Y axis.

4. A magnetic head according to claim 3, wherein the two legs of said excitation core are formed in a step-like shape such that a distance, as measured in a direction of the X axis, between cross-sections of the two legs along a parallel plane parallel to said common flat plane is discontinuously decreased as the parallel plane is further separated from said common flat plane.

5. A magnetic head for simultaneously detecting a total induced voltage signal and a Barkhausen signal comprising:

a magnetic excitation head having a U-shaped excitation core of metallic soft magnetic material having two legs, each of which has an end plane adapted to face a surface of an object to be measured, and an excitation coil wound on the excitation core to be excited by a low frequency current; and first and second detection heads each having a detection core made of non-magnetic material or soft magnetic material and a detection coil wound on the detection core;

wherein end planes of the detection cores of the first and second detection heads, each of which end planes is to be close to the surface of the object, and the end planes of the two legs of the excitation core are arranged such that each of the end planes of the detection cores is disposed between the end planes of the two legs and all the end planes are substantially on a common flat plane, and when defining XY rectangular coordinates on the common flat plane such that an X axis of the XY coordinates is defined by a straight line passing through centers of gravity of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values $x_1$ and $y_1$ of the XY coordinates representing a position of a center of gravity of the end plane of the detection core of the first detection head satisfy $$0.2a \leq |x_1| \leq 0.5a,\ |y_1| \leq 0.8b,$$

and values $x_2$ and $y_2$ of the XY coordinates representing a position of a center of gravity of the end plane of the detection core of the second detection head satisfy $$|x_2|<0.2a,\ |y_2|\leq 0.8b,$$

where a is a distance between the first and second points and b is a maximum width of the end plane of each of the two legs measured in a direction parallel to the Y axis.

6. A magnetic head according to claim 5, wherein the two legs of said excitation core are formed in a step-like shape such that a distance, as measured in a direction of the X axis, between cross-sections of the two legs along a parallel plane parallel to said common flat plane is discontinuously decreased as the parallel plane is further separated from said common flat plane.

7. A magnetic head for detecting a total induced voltage signal comprising:

a magnetic excitation head having a U-shaped excitation core of soft magnetic material having two legs, each of which has an end plane adapted to face a surface of an object to be measured, and an excitation coil wound on the excitation core to be excited by a low frequency current; and a detection head having a detection core made of non-magnetic material or soft magnetic material and a detection coil wound on the detection core;

wherein an end plane of the detection core of the detection head, which is to be close to the surface of the object, and the end planes of the two legs of the excitation core are arranged such that the end plane of the detection core is disposed between the end planes of the two legs and all the end planes are substantially on a common flat plane, and when defining XY rectangular coordinates on the flat plane such that an X axis of the XY coordinates is defined by a straight line passing through centers of gravity, as defined hereinafter, of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values x and y of the XY coordinates representing a position of a center of gravity of the end plane of the detection core satisfy $$0.2a \leq |x| \leq 0.5a,\ |y| \leq 0.8b,$$

where a is a distance between the first and second points and b is a maximum width of the end plane of each of the two legs measured in a direction parallel to the Y axis; and the two legs of said excitation core are formed in a step-like shape such that a distance, as measured in a direction of the X axis, between cross-sections of the two legs along a plane parallel to said common flat plane is discontinuously decreased as the parallel plane is further separated from said common flat plane.

8. A magnetic head for detecting a Barkhausen signal comprising:

a magnetic excitation head having a U-shaped excitation core of soft magnetic material having two legs, each of which has an end plane adapted to face a surface of an object to be measured, and an excitation coil wound on the excitation core to be excited by a low frequency current; and a detection head having a detection core made of non-magnetic material or soft magnetic material and a detection coil wound on the detection core;

wherein an end plane of the detection core of the detection head, which is to be close to the surface of the object, and the end planes of the two legs of the excitation core are arranged such that the end plane of the detection core is disposed between the end planes of the two legs and all the end planes are substantially on a common flat plane, and when defining XY rectangular coordinates on the flat plane such that an X axis of the XY coordinates is defined by a straight line passing through centers of gravity of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values x and y of the XY coordinates representing a position of a center of gravity of the end plane of the detection core satisfy $|x|<0.2a, |y|\leq 0.8b$, where a is a distance between the first and second points and b is a maximum width of the end plane of each of the two legs measured in a direction parallel to the Y axis; and the two legs of said excitation core are formed in a step-like shape such that a distance, as measured in a direction of the X axis, between cross-sections of the two legs along a plane parallel to said common flat plane is discontinuously decreased as the parallel plane is further separated from said common flat plane.

9. A magnetic head for simultaneously detecting a total induced voltage signal and a Barkhausen signal comprising:

a magnetic excitation head having a U-shaped excitation core of soft magnetic material having two legs, each of which has an end plane adapted to face a surface of an object to be measured, and an excitation coil wound on the excitation core to be excited by a low frequency current; and first and second detection heads each having a detection core made of non-magnetic material or soft magnetic material and a detection coil wound on the detection core;

wherein end planes of the detection cores of the first and second detection heads, each of which end planes is to be close to the surface of the object, and the end planes of the two legs of the excitation core are arranged such that each of the end planes of the detection cores is disposed between the end planes of the two legs and all the end planes are substantially on a common flat plane, and when defining XY rectangular coordinates on the common flat plane such that an X axis of the XY coordinates is defined by a straight line passing through centers of gravity of the end planes of the two legs, an origin of the XY coordinates is a center of a line connecting first and second points which are intersections of the X axis with respective peripheries of the end planes of the two legs and a Y axis is defined by a line passing the origin perpendicularly to the X axis, values $x_1$ and $Y_1$ of the XY coordinates representing a position of a center of gravity of the end plane of the detection core of the first detection head satisfy $0.2a \leq |x_1| \leq 0.5a, |y_1| \leq 0.8b$, and values $x_2$ and $y_2$ of the XY coordinates representing a position of a center of gravity of the end plane of the detection core of the second detection head satisfy $|x_2|<0.2a, |y_2|\leq 0.8b$, where a is a distance between the first and second points and b is a maximum width of the end plane of each of the two legs measured in a direction parallel to the Y axis; and the two legs of said excitation core are formed in a step-like shape such that a distance, as measured in a direction of the X axis, between cross-sections of the two legs along a plane parallel to said common flat plane is discontinuously decreased as the parallel plane is further separated from said common flat plane.

10. A magnetic head comprising:

a magnetic excitation head having a U-shaped excitation core of soft magnetic material having two legs, each of which has an end plane adapted to face a surface of an object to be measured, and an excitation coil wound on the excitation core to be excited by a low frequency current; and a detecting device including at least one detection head having a detection core made of non-magnetic material or soft magnetic material and a detection coil wound on the detection core;

wherein an end plane of the detection core of the detection head, which is to be close to the surface of the object, and the end planes of the two legs of the excitation core are arranged such that the end plane of the detection core is disposed between the end planes of the two legs and all the end planes are substantially on a common flat plane, and a position of said detection head relative to said excitation core is selected such that when the magnetic head is disposed to face the surface of the object and an AC current of a predetermined frequency is supplied to the excitation coil, a ratio $V_B/V_A$ of an effective value $V_A$ of a total induced voltage signal to a Barkhausen signal voltage $V_B$ induced into the detection coil is at a predetermined value.

11. A magnetic head according to claim 10, wherein the predetermined value of $V_B/V_A$ satisfies $\frac{1}{3}<V_B/V_A \leq 1$.

12. A magnetic head according to claim 10, wherein the predetermined value of $V_B/V_A$ satisfies $0<V_B/V_A \leq \frac{1}{3}$ 13. A magnetic head according to claim 10, wherein said detecting device further includes a second detection head having substantially the same components as those of the first-mentioned detection head and positions of first and second detection heads relative to the excitation core are selected such that when the magnetic head is disposed to face the surface of the object and an AC current of a predetermined frequency is supplied to the excitation coil, a ratio $V_{1B}/V_{1A}$ of an effective value $V_{1A}$ of a total induced voltage signal to a Barkhausen signal voltage $V_{1B}$ induced into the detection coil of the first detection head satisfies $$\tfrac{1}{3} < V_{1B}/V_{1A} \leq 1$$

and a ratio $V_{2B}/V_{2A}$ of an effective value $V_{2A}$ of a total induced voltage signal to a Barkhausen signal voltage $V_{2B}$ induced into the detection coil of the second detection head satisfies $$0 < V_{2B}/V_{2A} \leq \tfrac{1}{3}.$$

14. A method of detecting a total induced voltage signal induced in an object, said method comprising the steps of:

locating a magnetic head, which has a U-shaped excitation core of metallic soft magnetic material having two legs and an excitation coil wound on the excitation core to be excited by a low frequency current, at a position where end planes of said two legs face a surface of an object to be measured, while separating said magnetic head from the surface of the object by a distance in a range of 0.05 to 4 mm inclusive;

locating at least one detection head, which has a core made of non-magnetic material or soft magnetic material and a detection coil wound on the core of said detection head, at a position where an end plane of the core of said detection head and the end planes of the legs of the excitation core are substantially on a common flat plane and said detection head is disposed in such a positional relationship with the excitation head that when defining on the common flat plane XY rectangular coordinates, of which an X axis is defined by a straight line passing through centers of gravity of the end planes of the two legs, an origin is a center of a line connecting first and second points which are intersections of the X axis with respective peripheries of the end planes of the two legs and a Y axis is defined by a line passing the origin perpendicularly to the X axis, values x and y of the XY coordinates representing a position of a center of gravity of the end plane of the core of the detection head satisfy $$0.2a \leq |x| \leq 0.5a, \ |y| \leq 0.8b,$$

where a is a distance between the first and second points and b is a maximum width of the end plane of each of the two legs measured in a direction parallel to the Y axis;

supplying an AC current or a predetermined frequency to said excitation coil so as to generate magnetic flux flowing through the excitation core and the object; and measuring a total induced voltage signal induced in the detection coil of said detection head due to the magnetic flux flowing through the object.

15. A method according to claim 14, wherein the end plane of each of the two legs of said excitation core is disposed in parallel to the surface of the object.

16. A method of detecting a Barkhausen signal induced in an object, said method comprising the steps of:

locating a magnetic head, which has a U-shaped excitation core of metallic soft magnetic material having two legs and an excitation coil wound on the excitation core to be excited by a low frequency current, at a position where end planes of said two legs face a surface of an object to be measured, while separating said magnetic head from the surface of the object by a distance in a range of 0.05 to 4 mm inclusive;

locating at least one detection head, which has a core made of non-material or soft magnetic material and a detection coil wound on the core of said detection head, at a position where an end plane of the core of said detection head and the end planes of the legs of the excitation core are substantially on a common flat plane and said detection head is disposed in such a positional relationship with the excitation head that when defining on the common flat plane XY rectangular coordinates, of which an X axis is defined by a straight line passing through centers of gravity of the end planes of the two legs, an origin is a center of a line connecting first and second points which are intersections of the X axis with respective peripheries of the end planes of the two legs and a Y axis is defined by a line passing the origin perpendicularly to the X axis, values $x_1$ and $y_1$ of the XY coordinates representing a position of a center of gravity of the end plane of the core of the detection head satisfy $$|x_1| < 0.2a, \ |y_1| \leq 0.8b,$$

where a is a distance between the first and second points and b is a maximum width of the end plane of each of the two legs measured in a direction parallel to the Y axis;

supplying an AC current of a predetermined frequency to said excitation coil so as to generate magnetic flux flowing through the excitation core and the object; and measuring a Barkhausen signal induced in the detection coil of said detection head due to the magnetic flux flowing through the object.

17. A method according to claim 16, wherein the end plane of each of the two legs of said excitation core is disposed in parallel to the surface of the object.

18. A method of simultaneously detecting a total induced voltage signal and a Barkhausen signal induced in an object, said method comprising the steps of:

locating a magnetic head, which has a U-shaped excitation core of metallic soft magnetic material having two legs and an excitation coil wound on the excitation core to be excited by a low frequency current, at a position where end planes of said two legs face a surface of an object to be measured, while separating said magnetic head from the surface of the object by a distance in a range of 0.05 to 4 mm inclusive;

locating first and second detection heads, each of which has a core made of non-magnetic material or soft magnetic material and a detection coil wound on the core of said detection head, at respective positions where end planes of the respective cores of said first and second detection heads and the end planes of the less of the excitation core are substantially on a common flat plane, said first and second detection heads are disposed in such a positional relationship with the excitation head that when defining on the common flat plane XY rectangular coordinates, of which an X axis is defined by a straight line passing through centers of gravity of the end planes of the two legs, an origin is a center of a line connecting first and second points which are intersections of the X axis with respective peripheries of the end planes of the two legs and a Y axis is defined by a line passing the origin perpendicularly to the X axis, values $x_1$ and $y_1$ of the XY coordinates representing a position of a center of gravity of the end plane of the core of the first detection head satisfy $$0.2a \leq |x_1| \leq 0.5a, |y_1| \leq 0.8b,$$

and values $x_2$ and $y_2$ of the XY coordinates representing a position of a center of gravity of the end plane of the core of the second detection head satisfy $$|x_2| < 0.2a, |y_2| \leq 0.8b,$$

where a is a distance between the first and second points and b is a maximum width of the end plane of each of the two legs measured in a direction parallel to the Y axis;

supplying an AC current of a predetermined frequency to said excitation coil so as to generate magnetic flux flowing through the excitation core and the object;

measuring a total voltage signal induced in the detection coil of said first detection head due to the magnetic flux flowing through the object; and measuring a Barkhausen signal induced in the detection coil of said second detection head due to the magnetic flux flowing through the object.

19. A method according to claim 18, wherein the end plane of each of the two legs of said excitation core is disposed in parallel to the surface of the object.

* * * * *